(12) United States Patent
Suzuki et al.

(10) Patent No.: US 8,975,365 B2
(45) Date of Patent: Mar. 10, 2015

(54) CAGE-SHAPED CYCLOPENTANOIC DIANHYDRIDE, METHOD FOR PRODUCTION THEREOF, AND POLYIMIDE

(71) Applicant: Nissan Chemical Industries, Ltd., Tokyo (JP)

(72) Inventors: Hideo Suzuki, Funabashi (JP); Takahiro Noda, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 14/144,934

(22) Filed: Dec. 31, 2013

(65) Prior Publication Data

US 2014/0114027 A1 Apr. 24, 2014

Related U.S. Application Data

(62) Division of application No. 13/263,456, filed as application No. PCT/JP2010/056222 on Apr. 6, 2010, now Pat. No. 8,658,743.

(30) Foreign Application Priority Data

Apr. 10, 2009 (JP) ................. 2009-095953

(51) Int. Cl.
| | |
|---|---|
| C08G 69/26 | (2006.01) |
| C08G 69/40 | (2006.01) |
| C08G 73/10 | (2006.01) |
| C07C 61/06 | (2006.01) |
| C07C 51/09 | (2006.01) |
| C07C 67/08 | (2006.01) |
| C07C 67/333 | (2006.01) |
| C07D 493/04 | (2006.01) |
| C07D 493/22 | (2006.01) |

(52) U.S. Cl.
CPC ................ *C07C 61/06* (2013.01); *C07C 51/09* (2013.01); *C07C 67/08* (2013.01); *C07C 67/333* (2013.01); *C07D 493/04* (2013.01); *C07D 493/22* (2013.01); *C08G 73/105* (2013.01); *C08G 73/1075* (2013.01); *C08G 73/1078* (2013.01); *C08G 69/26* (2013.01); *C08G 69/40* (2013.01); *C07C 2101/08* (2013.01)
USPC ............................ 528/353; 528/185; 528/188

(58) Field of Classification Search
USPC ........... 525/436; 562/504; 528/185, 288, 188, 528/353; 560/122
See application file for complete search history.

(56) References Cited

U.S. PATENT DOCUMENTS

| | | | |
|---|---|---|---|
| 4,454,310 A | 6/1984 | Oka et al. | |
| 6,364,465 B1 | 4/2002 | Chandrasekaran | |
| 2009/0012318 A1 | 1/2009 | Suzuki et al. | |
| 2009/0018307 A1 | 1/2009 | Katayama et al. | |

FOREIGN PATENT DOCUMENTS

| | | |
|---|---|---|
| JP | 58-208322 A | 12/1983 |
| JP | 2-24294 B2 | 5/1990 |
| JP | 7-2728 A | 1/1995 |
| JP | 9-29983 A | 2/1997 |
| JP | 2006-232960 A | 9/2006 |
| JP | 2009-19105 A | 1/2009 |
| JP | 2009-57323 A | 3/2009 |
| WO | WO 2006/043519 A1 | 4/2006 |

OTHER PUBLICATIONS

International Search Report, dated May 18, 2010, for International Application No. PCT/JP2010/056222.
Somokawa et al., "Syntheses of Tetrasubstituted Cyclopentanes", Organic Preparations and Procedures Int., vol. 25, No. 4, pp. 449-456, 1993.

*Primary Examiner* — Kristin Vajda
(74) *Attorney, Agent, or Firm* — Birch, Stewart, Kolasch & Birch, LLP

(57) ABSTRACT

A cage 1,2,3,4-cyclopentanetetracarboxylic acid (1,3:2,4)-dianhydride compound represented by formula [1], and a polyimide obtained by condensing the compound with a diamine. With the compound, it is possible to provide a polyimide which shows no absorption in the ultraviolet region and is highly transparent to light, has high insulating properties, has improved heat resistance and processability, and has excellent solubility in organic solvents.

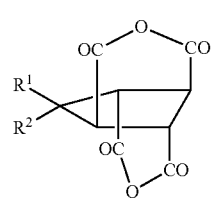

[1]

(In formula [1], $R^1$ and $R^2$ each independently represents a hydrogen atom, a halogen atom, or a $C_{1-10}$ alkyl.)

8 Claims, 6 Drawing Sheets

CAGE-SHAPED CYCLOPENTANOIC DIANHYDRIDE, METHOD FOR PRODUCTION THEREOF, AND POLYIMIDE

This application is a Divisional of co-pending application Ser. No. 13/263,456, filed on Jan. 9, 2012, which is the National Phase of International Application No. PCT/JP2010/056222 filed on Apr. 6, 2010, which claims priority to Japanese Patent Application No. 2009-095953 filed Apr. 10, 2009, all of which are hereby expressly incorporated by reference into the present application.

TECHNICAL FIELD

The present invention relates to a cage-shaped cyclopentanoic dianhydride, a method for production thereof, and a polyimide. More particularly, the present invention relates to a cage-shaped cyclopentanetetracarboxylic dianhydride as a monomer for the polyimide which is suitable for use as an optical material and the like and also to a method for production of the compound.

BACKGROUND ART

On account of their good mechanical strength, heat resistance, insulating properties, and solvent resistance, polyimides are in general use as an electronic material, such as protective material, insulating material, and color filter, for liquid crystal display units and semiconductors. They are also expected to find new uses as the material of optical waveguide for optical communications and as the material of substrates for mobile phones.

The recent remarkable development in these fields has come to require materials with more sophisticated properties than before. In other words, the polyimide used in these fields needs not only good heat resistance and solvent resistance but also many other properties, such as transparency, for individual applications.

The conventional polyimide in general use is a total aromatic polyimide which is obtained by polycondensation reaction between an aromatic tetracarboxylic dianhydride and an aromatic diamine. Unfortunately, because of its dark amber color, the total aromatic polyimide poses problems in application areas where high transparency is necessary. In practice, the total aromatic polyimide is insoluble in organic solvent, which makes it necessary to form its film from polyamic acid as its precursor by dehydrocyclization with heating.

One way of achieving good transparency is by the polycondensation reaction between an alicyclic tetracarboxylic dianhydride and an aromatic diamine, which yields a polyimide precursor, and the ensuing imidization of the precursor. This process is known to give a highly transparent polyimide with comparatively less discoloration (See Patent Documents 1 and 2).

Unfortunately, the polyamic acid and polyimide formed from an unsubstituted alicyclic tetracarboxylic dianhydride are hardly soluble in ordinary organic solvents and only soluble in high-boiling polar solvents. This necessitates heating at high temperatures for solvent removal in the film-forming process. Heating adversely affects any other organic materials constituting the organic EL element.

There has recently been reported a research on making the gas barrier film for the organic electroluminescence (EL) element from a polyimide polymerized from 1,2,3,4-cyclopentanetetracarboxylic acid-1:2,3:4-dianhydride (CPDA for short hereinafter) (See Patent Document 3).

Unfortunately, this polyimide still has room for improvement in heat resistance because of its low degree of polymerization and is not necessarily satisfactory in solubility in organic solvents.

PRIOR ART DOCUMENTS

Patent Documents

Patent Document 1: JP-B H02-24294
Patent Document 2: JP-A S58-208322
Patent Document 3: JP-A 2006-232960

SUMMARY OF THE INVENTION

Problems to be Solved by the Invention

The present invention was completed in view of the foregoing. It is an object of the present invention to provide an alicyclic tetracarboxylic dianhydride, a method for efficient and economical production thereof, and a polyimide formed therefrom, the compound being a monomer for the polyimide which excels in transparency without absorption in the UV region, insulating properties, heat resistance, processability, and solubility in organic solvents.

Means for Solving the Problems

The present inventors carried out extensive researches to achieve the foregoing object by paying attention to increasing the linearity of the main chain of the polyimide structure, thereby raising the degree of polymerization. As the result, they found a cage-shaped cyclopentanetetracarboxylic dianhydride as the monomer for the polyimide which, because of its good linearity, has a high degree of polymerization and excels in heat resistance and solubility in organic solvents. This finding led to the present invention.

The present invention covers the following.

1. A cage-shaped 1,2,3,4-cyclopentanetetracarboxylic acid-1,3:2,4-dianhydride represented by the formula [1].

[Chemical Formula 1]

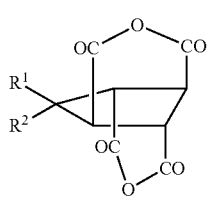

[1]

(where $R^1$ and $R^2$ independently denote a hydrogen atom, halogen atom, or $C_{1-10}$ alkyl group.)

2. The cage-shaped 1,2,3,4-cyclopentanetetracarboxylic acid-1,3:2,4-dianhydride as defined in Paragraph 1 above, wherein $R^1$ and $R^2$ each denotes a hydrogen atom.

3. A trans,trans,trans-1,2,3,4-cyclopentanetetracarboxylic acid represented by the formula [2].

[Chemical Formula 2]

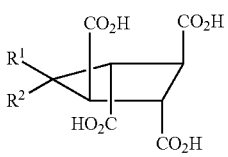

[2]

(where $R^1$ and $R^2$ independently denote a hydrogen atom, halogen atom, or $C_{1-10}$ alkyl group.)

4. A trans,trans,trans-1,2,3,4-cyclopentanetetracarboxylic tetraalkyl ester represented by the formula [3].

[Chemical Formula 3]

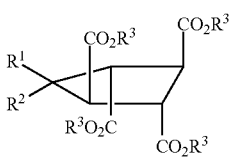

[3]

(where $R^1$ and $R^2$ independently denote a hydrogen atom, halogen atom, or $C_{1-10}$ alkyl group, and $R^3$ denotes a $C_{1-10}$ alkyl group.)

5. A method including
a first step of reacting cis,cis,cis-1,2,3,4-cyclopentanetetracarboxylic acid-1,2:3,4-dianhydride represented by the formula [4].

[Chemical Formula 4]

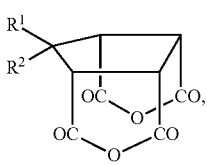

[4]

(where $R^1$ and $R^2$ independently denote a hydrogen atom, halogen atom, or $C_{1-10}$ alkyl group.)
with an alcohol represented by the formula [5]

$R^3OH$      [5]

(where $R^3$ denotes a $C_{1-10}$ alkyl group.)
in the presence of an acid catalyst, thereby giving cis,cis,cis-1,2,3,4-cyclopentanetetracarboxylic tetraalkyl ester represented by the formula [6]

[Chemical Formula 5]

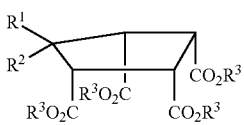

[6]

(where $R^1$, $R^2$, and $R^3$ are defined as above.)
a second step of isomerizing in the presence of a base catalyst the compound represented by the formula [6] above, which was obtained in the first step, thereby giving trans,trans,trans-1,2,3,4-cyclopentanetetracarboxylic tetraalkyl ester represented by the formula [3]

[Chemical Formula 6]

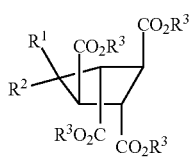

[3]

(where $R^1$, $R^2$, and $R^3$ are defined as above.)
a third step of decomposing with the help of an organic acid the compound represented by the formula [3] above, which was obtained in the second step, thereby giving trans,trans,trans-1,2,3,4-cyclopentanetetracarboxylic acid represented by the formula [2]

[Chemical Formula 7]

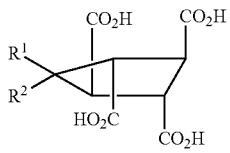

[2]

(where $R^1$ and $R^2$ are defined as above.)
and
a fourth step of dehydrating the compound represented by the formula [2] above, which was obtained in the third step, thereby giving a cage-shaped 1,2,3,4-cyclopentanetetracarboxylic acid-1,3:2,4-dianhydride represented by the formula [1].

[Chemical Formula 8]

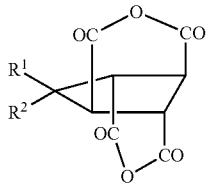

[1]

(where $R^1$ and $R^2$ are defined as above.)

6. The production method as defined in Paragraph 5, wherein the acid catalyst used in the first step is sulfuric acid.
7. The production method as defined in Paragraph 5, wherein the base catalyst used in the second step is metal alcoholate.
8. The production method as defined in Paragraph 7, wherein the base catalyst is potassium t-butoxide.
9. The production method as defined in Paragraph 5, wherein the isomerization in the second step is accomplished at 0 to 200° C.
10. The production method as defined in Paragraph 5, wherein the organic acid used in the third step is formic acid.
11. The production method as defined in Paragraph 5, wherein the decomposition with the help of organic acid is accomplished at 0 to 200° C.
12. The production method as defined in Paragraph 5, wherein the dehydration in the fourth step is accomplished with the help of an organic acid anhydride.

13. A polyamic acid which contains the repeating unit represented by the formula [7] below in an amount of at least 10 mol %.

[Chemical Formula 9]

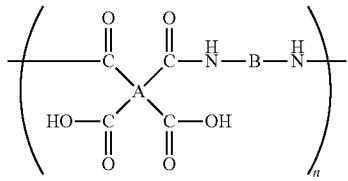
[7]

(where A denotes a tetravalent organic group represented by the formula [8] and B denotes a divalent organic group and n is an integer.)

[Chemical Formula 10]

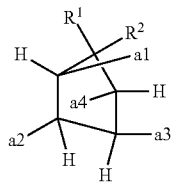
[8]

(where $R^1$ and $R^2$ independently denote a hydrogen atom, halogen atom, or $C_{1-10}$ alkyl group; and a1 to a4 denote the positions for bonding with the carbon atom of the carbonyl group in the formula [7], provided that bonding with the carboxyl group does not take place simultaneously at a1 and a3 and bonding with the carboxyl group does not take place simultaneously at a2 and a4.)

14. The polyamic acid as defined in Paragraph 13 wherein the $R^1$ and $R^2$ each is a hydrogen atom or methyl group.
15. The polyamic acid as defined in Paragraph 13 wherein the B is a divalent organic group derived from an alicyclic diamine or aliphatic diamine.
16. The polyamic acid as defined in Paragraph 13 or 14, wherein the B is at least one species selected from the divalent organic groups represented by the formulas [9] to [12].

[Chemical Formula 11]

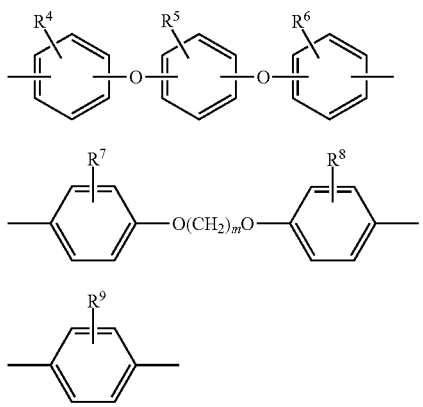
[9]

[10]

[11]

-continued

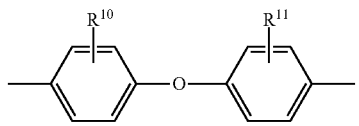
[12]

(where $R^4$ to $R^{11}$ independently denote a hydrogen atom, halogen atom, or $C_{1-10}$ alkyl group, and m is an integer of 1 to 10.)

17. The polyamic acid as defined in Paragraph 16, wherein the B is represented by the formula [13].

[Chemical Formual 12]

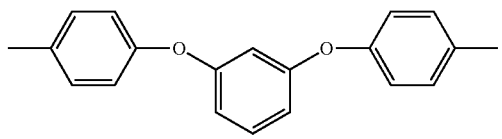
[13]

18. The polyamic acid as defined in Paragraph 16, wherein the B is represented by the formula [14].

[Chemical Formual 13]

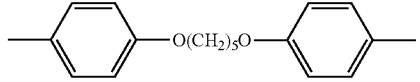
[14]

19. The polyamic acid as defined in Paragraph 16, wherein the B is represented by the formula [15].

[Chemical Formual 14]

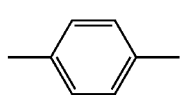
[15]

20. The polyamic acid as defined in Paragraph 16, wherein the B is represented by the formula [16].

[Chemical Formual 15]

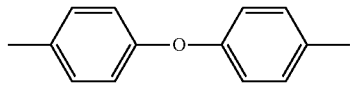
[16]

21. A polyimide which is obtained by cyclodehydration from any one of the polyamic acids defined in Paragraphs 13 to 20.

Advantageous Effect of the Invention

According to the present invention, there are provided a cage-shaped 1,2,3,4-cyclopentanetetracarboxylic acid-1,3:2,4-dianhydride ("cage" CPDA for short hereinafter) and a method for efficient production thereof, the compound giving a polyimide which has a high degree of polymerization and exhibits good heat resistance and high solubility in organic solvents. Owing to its improved heat resistance and good optical transparency without absorption in the UV region, the resulting polyimide is expected to find use as a protecting and insulating material for electronic devices such as liquid crystal displays and semiconductors and also as waveguide for optical communications.

EMBODIMENT FOR CARRYING OUT THE INVENTION

Figure 1:
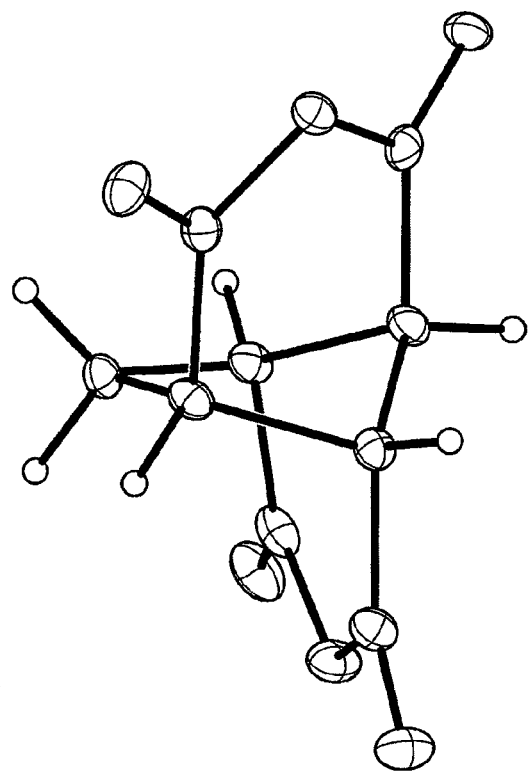
FIG. 1 is an X-ray ORTEP diagram of a single crystal of "cage" CPDA which was obtained in Example 4.
Figure 2:
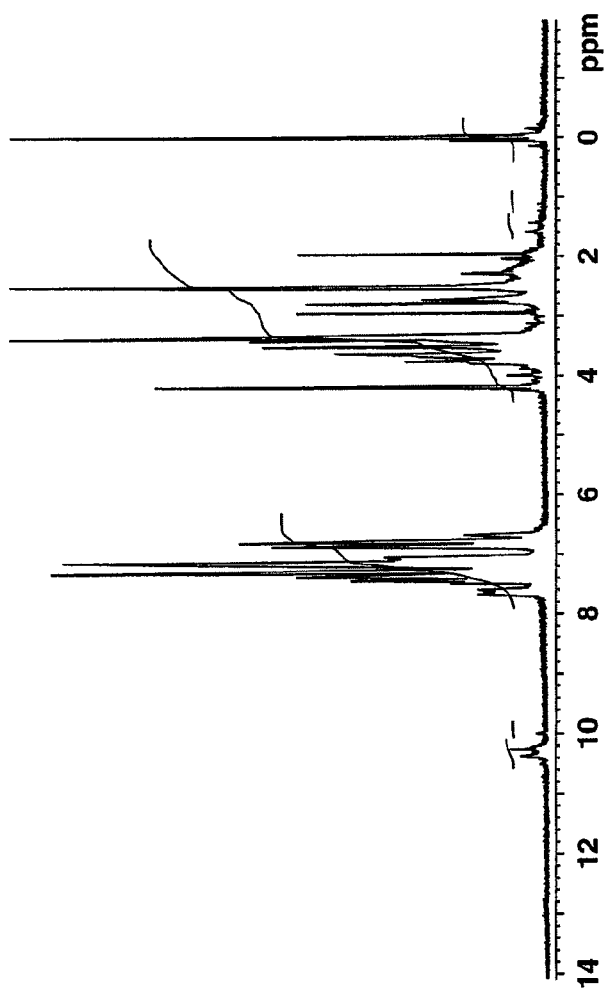
FIG. 2 is a $^1$H-NMR spectrum of "cage" CPDA-1,3-BAPB polyimide which was obtained in Example 5.
Figure 3:
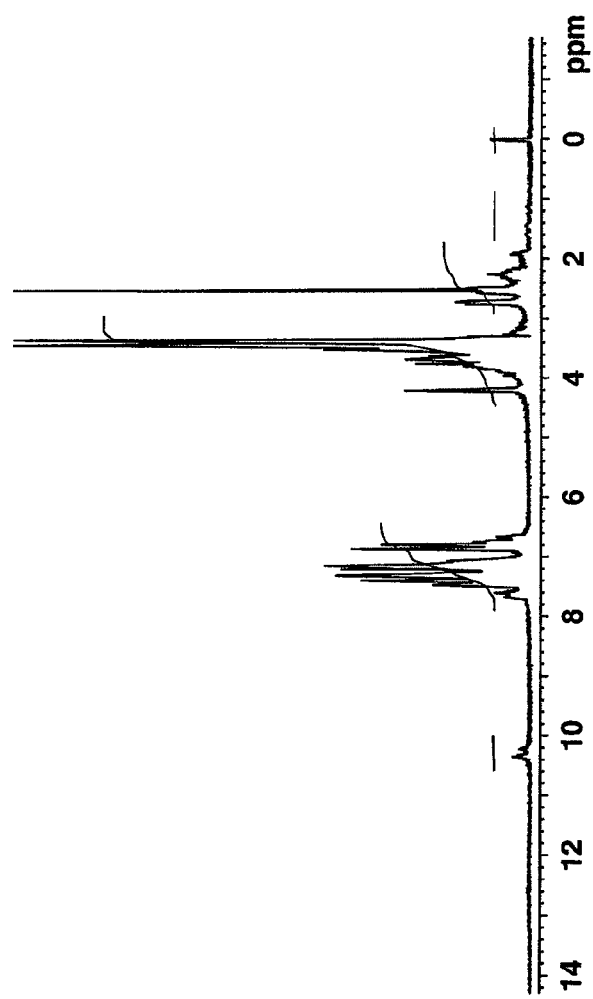
FIG. 3 is a $^1$H-NMR spectrum of "cage" CPDA-1,3-BAPB polyimide which was obtained in Example 6.
Figure 4:
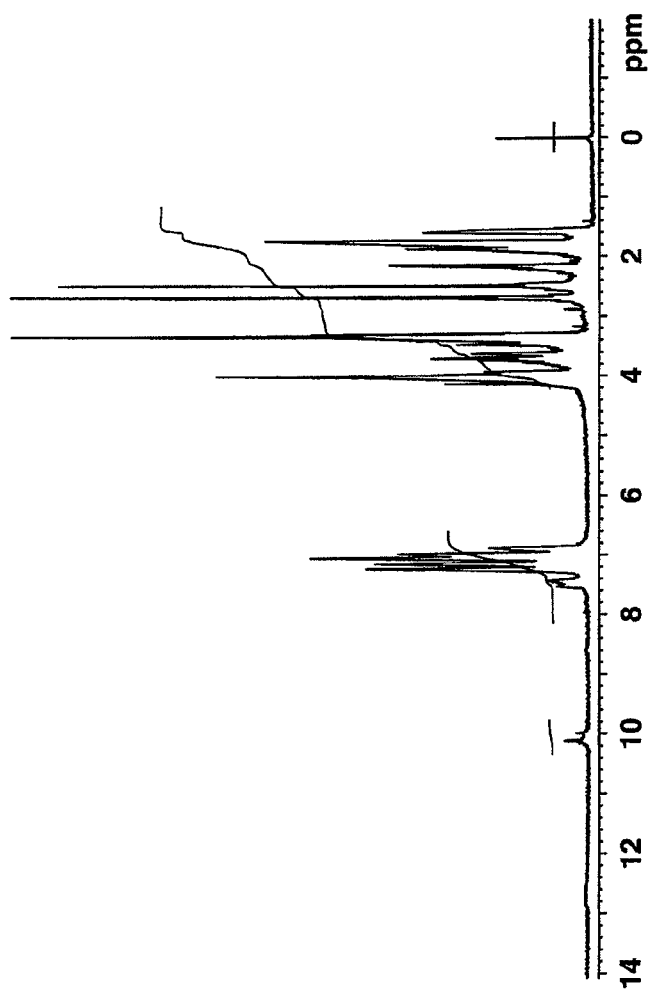
FIG. 4 is a $^1$H-NMR spectrum of "cage" CPDA-DPP polyimide which was obtained in Example 7.
Figure 5:
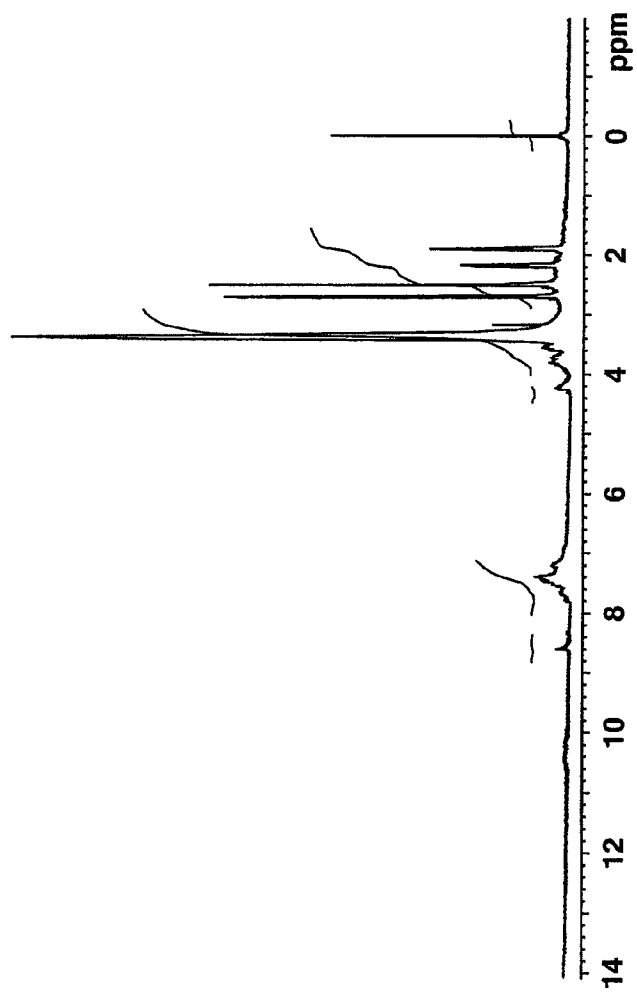
FIG. 5 is a $^1$H-NMR spectrum of "cage" CPDA-p-PDA polyimide which was obtained in Example 8.
Figure 6:
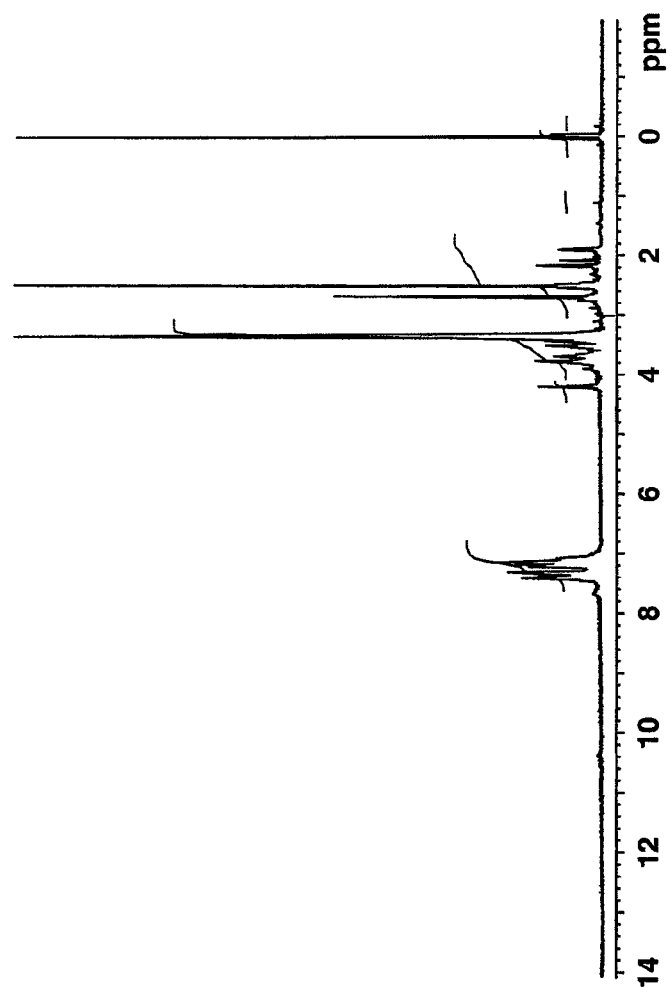
FIG. 6 is a $^1$H-NMR spectrum of "cage" CPDA-DDE polyimide which was obtained in Example 9.

A detailed description of the invention will follow, in which such symbols as n, i, s, t, and c stand for normal, iso, secondary, tertiary, and cyclo, respectively.

In the foregoing formulas, the halogen atom includes fluorine, chlorine, bromine, and iodine atoms.

The $C_{1-10}$ alkyl group includes linear, branched, and cyclic ones, as exemplified by methyl, ethyl, n-propyl, i-propyl, c-propyl, n-butyl, i-butyl, s-butyl, t-butyl, c-butyl, n-pentyl, 1-methyl-n-butyl, 2-methyl-n-butyl, 3-methyl-n-butyl, 1,1-dimethyl-n-propyl, c-pentyl, 2-methyl-c-butyl, n-hexyl, 1-methyl-n-pentyl, 2-methyl-n-pentyl, 1,1-dimethyl-n-butyl, 1-ethyl-n-butyl, 1,1,2-trimethyl-n-propyl, c-hexyl, 1-methyl-c-pentyl, 1-ethyl-c-butyl, 1,2-dimethyl-c-butyl, n-heptyl, n-octyl, n-nonyl, and n-decyl.

The "cage" CPDA according to the present invention can be produced by four steps shown in the following scheme.

A first step of reacting cis,cis,cis-1,2,3,4-cyclopentanetetracarboxylic acid-1,3:2,4-dianhydride (cis,cis,cis-CPDA for short hereinafter) with an alcohol in the presence of an acid catalyst, thereby giving cis,cis,cis-1,2,3,4-cyclopentanetetracarboxylic tetraalkyl ester (cis,cis,cis-TACP for short hereinafter); a second step of isomerizing in the presence of a base catalyst the cis,cis,cis-TACP, thereby giving trans,trans,trans-1,2,3,4-cyclopentanetetracarboxylic tetraalkyl ester (trans,trans,trans-TACP for short hereinafter); a third step of decomposing the trans,trans,trans-TACP, thereby giving trans,trans,trans-1,2,3,4-cyclopentanetetracarboxylic acid (trans,trans,trans-CPTC for short hereinafter); and a fourth step of dehydrating the trans,trans,trans-CPTC, thereby giving the "cage" CPDA.

[Chemical Formula 16]

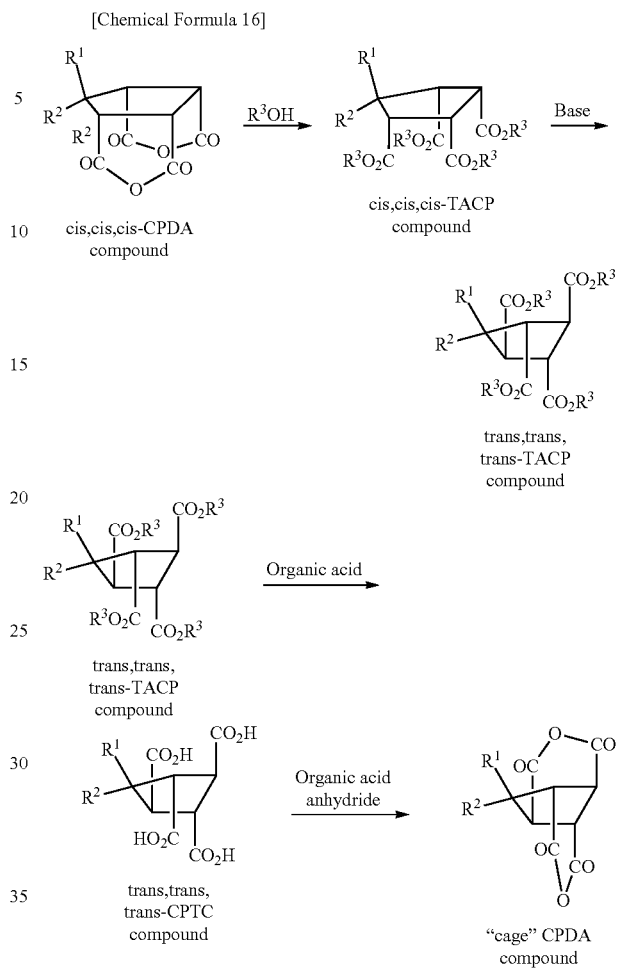

(where $R^1$ to $R^3$ are defined as above.)

Incidentally, the cis,cis,cis-CPDA as the raw material in the first step may be synthesized by the process shown in the following scheme.

That is, Diels-Alder reaction between cyclopentadiene (CPD) and maleic anhydride, which gives 5-norbornene-2,3-dicarboxylic anhydride (NDA). Then, the oxidation of NDA for conversion into 1,2,3,4-cyclopentanetetracarboxylic acid (CPTC). Finally, the dehydration of CPTC to give the desired cis,cis,cis-CPDA.

[Chemical Formula 17]

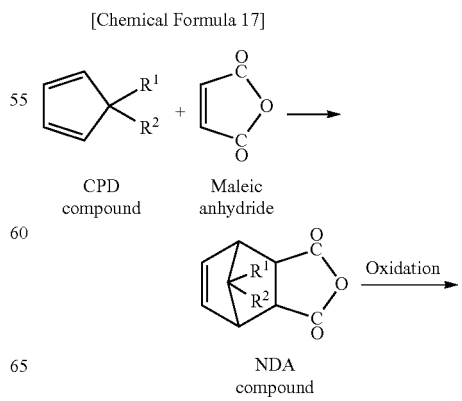

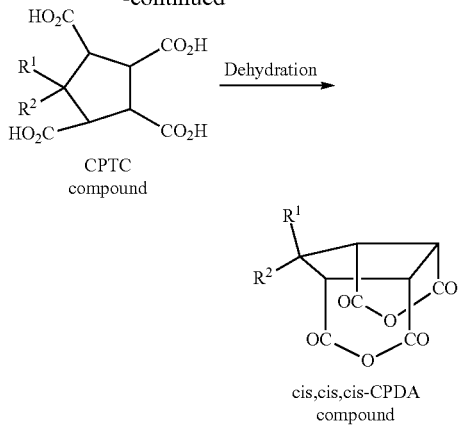

(where $R^1$ and $R^2$ are defined as above.)

Typical examples of the CPD include cyclopentadiene, 1-methyl-2,4-cyclopentadiene, 1-ethyl-2,4-cyclopentadiene, 1-n-propyl-2,4-cyclopentadiene, 1-n-butyl-2,4-cyclopentadiene, 1-n-octyl-2,4-cyclopentadiene, 1-n-nonyl-2,4-cyclopentadiene, 1-n-decyl-2,4-cyclopentadiene, 1,1-dimethyl-2,4-cyclopentadiene, 1,1-diethyl-2,4-cyclopentadiene, 1,1-di(n-decyl)-2,4-cyclopentadiene, 1-fluoro-2,4-cyclopentadiene, 1,1-difluoro-2,4-cyclopentadiene, 1-chloro-2,4-cyclopentadiene, 1,1-dichloro-2,4-cyclopentadiene, 1-bromo-2,4-cyclopentadiene, and 1,1-dibromo-2,4-cyclopentadiene.

Incidentally, the cis,cis,cis-CPDA to be produced from cyclopentadiene is commercially available, and any commercial product may be used as such.

[1] The First Step for Esterification Reaction

The esterification employs any one of such $C_{1-10}$ alkyl alcohols as methanol, ethanol, n-propanol, i-propanol, n-octanol, and n-decanol. Of these alcohols, methanol is economically preferable. It should be used in an amount (by weight) 2 to 30 times, preferably 3 to 10 times, the reactant.

The esterification also employs an acid catalyst selected from inorganic acids, such as hydrochloric acid and sulfuric acid, solid acids, such as heteropoly acid and cation exchange resin. Of these acids, sulfuric acid is preferable. It should be used in an amount of 0.1 to 20 wt %, preferably 1 to 10 wt %, of the reactant.

The esterification should be carried out at 20 to 200° C., preferably 50 to 150° C., in the vicinity of the boiling point of the alcohol.

The progress of esterification can be checked by gas chromatography. When it is found that the reactant has disappeared after esterification with the help of sulfuric acid as an acid catalyst, the reaction product is condensed and the resulting oily condensate is extracted with ethyl acetate and water. The thus obtained organic layer is washed with water and dried to give the desired cis,cis,cis-TACP.

[2] The Second Step for Isomerization

The isomerization employs any one of such base catalysts as alkali metal or alkaline earth metal in the form of alcoholate, carbonate, hydroxide, or oxide. Of these compounds, alcoholate is preferable.

The alkali metal includes lithium, sodium, and potassium, and the alkaline earth metal includes magnesium, calcium, and barium.

Preferable among alcoholates are sodium methoxide, sodium ethoxide, sodium t-butoxide, potassium methoxide, potassium ethoxide, and potassium t-butoxide. Particularly preferable among them are sodium methoxide and potassium t-butoxide.

The base catalyst should be used in an amount of 0.1 to 50 mol %, preferably 0.5 to 20 mol %, of the reactant.

The solvent for isomerization should preferably be an alcohol, particularly a lower alcohol such as methanol, ethanol, n-propanol, and i-propanol. Of these alcohols, methanol is preferable. It should be used in an amount (by weight) 3 to 30 times, preferably 5 to 10 times, the reactant.

The reaction temperature for isomerization should preferably be 0 to 200° C., particularly 20 to 150° C.

After the completion of isomerization, the reaction product is condensed and the resulting residue is extracted with ethyl acetate and water. The resulting extract is acidified with 35% hydrochloric acid for separation of the organic layer. The thus obtained organic layer is condensed to give crude trans,trans,trans-TACP. This crude product is purified by silica gel chromatography to give pure trans,trans,trans-TACP.

[3] The Third Step for Acid Decomposition

The third step employs an acid selected from inorganic acids, such as hydrochloric acid, sulfuric acid, and phosphoric acid, fatty acids, such as formic acid, acetic acid, and propionic acid, and sulfonic acids, such as methanesulfonic acid, ethansulfonic acid, and trifluoromethanesulfonic acid. Of these acids, formic acid is preferable because it is easy to use. It should be used in an amount more than 4 mol equivalents for the reactant.

Formic acid should be used in an excess amount (10 to 100 mol equivalent) because formic ester that occurs as a by-product is distilled away together with formic acid to promote reactions.

The above-mentioned acid should preferably be used in combination with benzenesulfonic acid or p-toluenesulfonic acid, with the latter being more desirable. The amount of such additional acid should be 0.1 to 10 wt %, preferably 0.5 to 5 wt %, of the reactant.

This reaction should be continued until the reactant disappears (as indicated by the $^1$H-NMR spectrum), with the acid ester as a by-product distilled away.

The reaction temperature should preferably be 0 to 200° C.

After the completion of reaction, the reaction liquid is condensed and the condensate is dissolved with heating in acetonitrile added thereto. The resulting solution is slightly condensed and then ice-cooled for crystallization. The crystals are filtered off and washed with ethyl acetate and finally vacuum-dried to give the desired trans,trans,trans-CPTC.

Residual p-toluenesulfonic acid may be removed as follow, if it should exist. The product is dissolved in ethyl acetate and a small amount of water added thereto. The organic layer is condensed and the residue is dissolved with heating in acetonitrile added thereto. The resulting solution is slightly condensed and ice-cooled for crystallization. The crystals are filtered off, washed with ethyl acetate, and vacuum-dried.

[4] The Fourth Step for Dehydration

This step employs a dehydrating agent, such as aliphatic carboxylic acid anhydride, 1,3-dicyclohexylcarbodiimide (DCC), and 2-chloro-1,3-dimethylimidazolium chloride (DMC). The first one, which is typically exemplified by acetic anhydride, is preferable because of its low price. It should be used in an amount of 2 to 50 equivalents, preferably 2 to 10 equivalents, for the reactant.

This step may employ the dehydrating agent in an excess amount as a solvent or employ any organic solvent not involved directly with the reaction.

Examples of such an organic solvent include aromatic hydrocarbons, such as toluene and xylene, halogenated hydrocarbons, such as 1,2-dichloroethane and 1,2-dichloropropane, and 1,4-dioxane. It should be used in an amount (by weight) 1 to 20 times, preferably 1 to 10 times, the reactant.

The reaction temperature for this step is usually 50 to 200° C., preferably 60 to 150° C., in the vicinity of the boiling point of the dehydrating agent or solvent.

The reaction time for this step is 0.1 to 10 hours, preferably 0.2 to 5 hours, which varies depending on the reaction temperature.

After the completion of reaction, the reaction product is freed of the dehydrating agent (together with the solvent if necessary) by distillation. In this way there is obtained "cage" CPDA in high purity. It may be further purified by recrystallization according to need.

If the third step employs formic acid, the third and fourth steps may be combined into one step. In this case, the reaction mixture obtained in the third step undergoes dehydration in such a way that formic acid and acetic acid (that occurs as a by-product if acetic anhydride is used as the dehydrating agent) are distilled away together with the optional organic solvent. In this way the desired "cage" CPDA is obtained with a high degree of conversion.

The above-mentioned reactions may be carried out batch-wise or continuously, with or without compression.

The "cage" CPDA of the present invention, which has been obtained as mentioned above, may undergo polycondensation with a diamine to give a polyamic acid represented by the formula [7] below, which subsequently undergoes dehydrocyclization with heating or catalyst, so that it is converted into its corresponding polyimide.

[Chemical Formula 18]

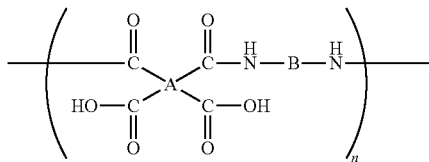

[7]

(where A denotes a tetravalent organic group represented by the formula [8] and B denotes a divalent organic group and n is an integer.)

[Chemical Formula 19]

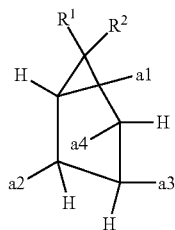

[8]

(where $R^1$ and $R^2$ are defined as above; and a1 to a4 denote the positions for bonding in the formula [7], provided that bonding with the carboxyl group does not take place simultaneously at a1 and a3 and bonding with the carboxyl group does not take place simultaneously at a2 and a4.)

The cyclopentane skeleton represented by the formula [8] has the trans-trans-trans conformation indicated by a1 to a4.

In the formula [8] above, $R^1$ and $R^2$ independently denote a hydrogen atom, halogen atom, and $C_{1-10}$ alkyl group, with a hydrogen atom and a methyl group being preferable. In other words, the "cage" CPDA as the desirable starting material is any of cage-shaped 1,2,3-4-cyclopentanetetracarboxylic acid-1,3:2,4-dianhydride, cage-shape 5-methyl-1,2,3,4-cyclopentanetetracarboxylic acid-1,3:2,4-dianhydride, and cage-shaped 5,5-dimethyl-1,2,3,4-cyclopentanetetracarboxylic acid-1,3:2,4-dianhydride.

According to the present invention, the polyamic acid contains the repeating unit represented by the formula [7] in an amount more than 10 mol %. However, the content of the repeating unit should be more than 50 mol %, preferably more than 80 mol %, or 100 mol %, in order for the resulting polyimide to have high transparency and good solubility in organic solvents as intended in the present invention.

The diamine for polycondensation is not specifically restricted. Any ones conventionally used for polyimide synthesis are acceptable. Their typical examples are listed below.

Aromatic diamines, such as p-phenylenediamine, m-phenylenediamine, 2,5-diaminotoluene, 2,6-diaminotoluene, 1,3-bis(4,4'-aminophenoxy)benzene, 4,4'-diamino-1,5-phenoxypentane, 4,4'-diaminobiphenyl, 3,3'-dimethyl-4,4'-diaminobiphenyl, 3,3'-dimethoxy-4,4'-diaminobiphenyl, 4,4'-diaminodiphenyl ether, 4,4'-diaminophenylmethane, 2,2'-diaminodiphenylpropane, bis(3,5-diethyl-4-aminophenyl)methane, diaminodiphenylsulfone, diaminobenzophenone, diaminonaphthalene, 1,4-bis(4-aminophenoxy)benzene, 1,4-bis(4-aminophenyl)benzene, 9,10-bis(4-aminophenyl)anthracene, 1,3-bis(4-aminophenoxy)benzene, 4,4'-bis(4-aminophenoxy)diphenylsulfone, 2,2-bis[4-(4-aminophenoxy)phenyl]propane, and 2,2'-trifluoromethyl-4,4'-diaminobiphenyl.

Alicyclic diamines, such as 1,4-diaminocyclohexane, 1,4-cyclohexanebis(methylamine), 4,4'-diaminodicyclohexylmethane, bis(4-amino-3-methylcyclohexyl)methane, 3(4),8(9)-bis(aminomethyl)tricyclo[5.2.1.0$^{2,6}$]decane, 2,5(6)-bis(aminomethyl)bicyclo[2.2.1]heptane, 1,3-diaminoadamantane, 3,3'-diamino-1,1'-biadamantyl, and 1,6-diaminoadamantane(1,6-aminopentanecyclo-[7.3.1.1$^{4,12}$,0$^{2,7}$,0$^{6,11}$]tetradecane.

Aliphatic diamines, such as tetramethylenediamine and hexamethylenediamine.

Incidentally, these diamines may be used alone or in combination with one another.

Of these diamines, alicyclic and aliphatic ones are desirable because the resulting polyimide obtained via the polyamic acid excels in transparency.

The polyamic acid according to the present invention should have the diamine residue B whose preferable examples are represented by the formulas [9] to [12] below, where $R^4$ to $R^{11}$ independently denote a hydrogen atom, halogen atom, or $C_{1-10}$ alkyl group, with a hydrogen atom being desirable.

Incidentally, in the formula [10], m denotes an integer of 1 to 10, preferably 1 to 5. Therefore, the diamine residue B represented by any one of the formulas [13] to [16] below is more desirable.

[Chemical Formula 20]

[9]
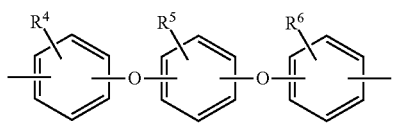

[10]
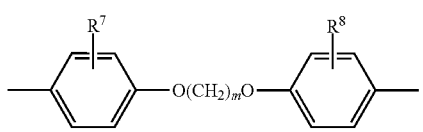

[11]
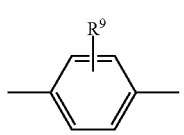

[12]

[Chemical Formula 21]

[13]
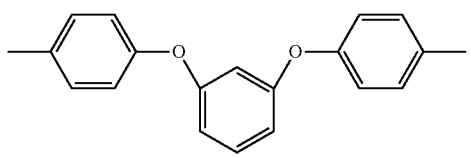

[14]
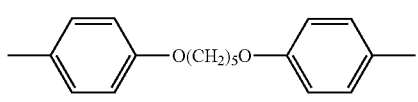

[15]

[16]
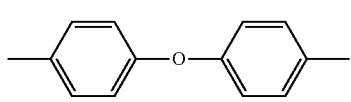

As mentioned above, the present invention requires that the tetracarboxylic acid dianhydride should contain the "cage" CPDA represented by the formula [1] in an amount of at least 10 mol %. However, it may be used in combination with a tetracarboxylic acid or a derivative thereof which is used for ordinary polyimide synthesis, so long as the content of the "cage" CPDA is higher than 10 mol %.

Typical examples of the tetracarboxylic acid include alicyclic tetracarboxylic acids, dianhydrides thereof, and dicarboxylic acid diacid halides thereof, such as 1,2,3,4-cyclobutanetetracarboxylic acid, 2,3,4,5-tetrahydrofurantetracarboxylic acid, 1,2,4,5-cyclohexanetetracarboxylic acid, 3,4-dicarboxy-1-cyclohexylsuccinic acid, 3,4-dicarboxy-1,2,3,4-tetrahydro-1-naphthalenesuccinic acid, and bicyclo[3.3.0]octane-2,4,6,8-tetracarboxylic acid.

Additional examples include aromatic tetracarboxylic acids, dianhydrides thereof, and dicarboxylic acid diacid halides thereof, such as pyromellitic acid, 2,3,6,7-naphthalenetetracarboxylic acid, 1,2,5,6-naphthalenetetracraboxylic acid, 1,4,5,8-naphthalenetetracraboxylic acid, 2,3,6,7-anthracenetetracarboxylic acid, 1,2,5,6-anthracenetetracarboxylic acid, 3,3',4,4'-biphenyltetracarboxylic acid, 2,3,3',4-biphenyltetracarboxylic acid, bis(3,4-dicarboxyphenyl)methane, 3,3',4,4'-benzophenonetetracarboxylic acid, bis(3,4-dicarboxyphenyl)methane, 2,2-bis(3,4-dicarboxyphenyl) propane, 1,1,1,3,3,3-hexafluoro-2,2-bis(3,4-dicarboxyphenyl)propane, bis(3,4-dicarboxyphenyl) dimethylsilane, bis(3,4-dicarboxyphenyl)diphenylsilane, 2,3,4,5-pyridinetetracarboxylic acid, and 2,6-bis(3,4-dicarboxyphenyl)pyridine. Incidentally, the foregoing tetracarboxylic acids may be used alone or in combination with one another.

The polyamic acid according to the present invention may be obtained in any way without specific restrictions. One known way is by reaction of a tetracarboxylic dianhydride and/or a derivative thereof with a diamine for polymerization. One simple way is by reaction between a tetracarboxylic dianhydride and a diamine which are mixed in an organic solvent.

The organic solvent used for this purpose includes, for example, m-cresol, N-methyl-2-pyrrolidone (NMP), N,N-dimethylformamide (DMF), N,N-dimethylacetamide (DMAc), N-methylcaprolactam, dimethylsufoxide (DMSO), tetramethylurea, pyridine, dimethylsulfone, hexamethylphosphoramide, and γ-butyrolactone. These solvents may be used alone or in combination with one another. Incidentally, they may be used in combination with any solvent incapable of dissolving the polyamic acid so long as the mixed solvent gives a homogenous solution.

The solution polymerization may be carried out at any arbitrary temperature ranging from −20° C. to 150° C., preferably from −5° C. to 100° C. The resulting polyamic acid varies in molecular weight depending on the molar ratio of the tetracarboxylic dianhydride and the diamine involved in polymerization. Its molecular weight increases according as the molar ratio approaches one, as in the case of ordinary polycondensation. The molar ratio of total tetracarboxylic dianhydrides to total diamines should preferably be from 0.8 to 1.2.

There are several methods for dissolving the tetracarboxylic dianhydride and the diamine in an organic solvent. One method involves dispersion or dissolution of the diamine in an organic solvent and addition of the tetracarboxylic dianhydride (as such or dissolved or dispersed in an organic solvent) to the solution of the diamine. In another method, the foregoing steps are carried out in a reverse order or alternately. Any one of them may be employed in the present invention.

In the case where more than one species of tetracarboxylic dianhydride or diamine are used, they may be put into reaction individually and sequentially or all together in the form of previously prepared mixture.

The polyamic acid obtained as mentioned above subsequently undergoes dehydrocyclization to give the polyimide of the present invention. The ratio of conversion from polyamic acid to polyimide is defined as the imidizing ratio. The present invention does not necessarily require the imidizing ratio to be 100% but permits it to vary from 1% to 100%.

The present invention does not restrict the method for dehydrocyclization of the polyamic acid. Heating or catalyst may be employed as in the case of ordinary polyamic acid.

Dehydrocyclization by heating may be accomplished at any temperature from 100° C. to 300° C., preferably from 120° C. to 250° C.

Dehydrocyclization by catalyst may be accomplished in the presence of an organic base (such as pyridine and triethylamine) and acetic anhydride at any temperature from −20° C.

to 200° C. The resulting polyamic polymer solution may be used as such or after dilution. An alternative method involves recovery of polyamic acid from the polyamic polymer solution and dissolution in an adequate organic solvent. The organic solvent for this purpose is the same one as mentioned above which is used for polymerization of polyamic acid.

The thus obtained solution of (or containing) polyimide may be used as such or undergo the subsequent step, in which it is given a poor solvent (such as methanol and ethanol) for precipitation of polymer and the precipitates are separated. The separated precipitates (in powder form) may be used as such or after redissolution in an adequate solvent.

The solvent for redissolution is not specifically restricted so long as it is capable of dissolving the resulting polymer. It includes, for example, m-cresol, 2-pyrrolidone, NMP, N-ethyl-2-pyrrolidone, N-vinyl-2-pyrrolidone, DMAc, DMF, and γ-butyrolactone.

Any solvent which does not dissolve the polymer when used alone may be used in combination with the foregoing solvents within an amount not harmful to solubility. Examples of such solvents are listed below.

Ethylcellosolve, butylcellosolve, ethylcarbitol, butylcarbitol, ethylcarbitol acetate, ethylene glycol, 1-methoxy-2-propanol, 1-ethoxy-2-propanol, 1-butoxy-2-propanol, 1-phenoxy-2-propanol, propylene glycol monoacetate, propylene glycol diacetate, propylene glycol-1-monomethy ether-2-acetate, propylene glycol-1-monoethyl ether-2-acetate, dipropylene glycol, 2-(2-ethoxypropoxy)propanol, methyl lactate, ethyl lactate, n-propyl lactate, n-butyl lactate, and isoamyl lactate.

The polyamic acid or polyimide according to the present invention is not specifically restricted in molecular weight. Their molecular weight should be properly selected according to their usage. With an excessively small molecular weight, they will yield a material poor in strength. With an excessively large molecular weight, they will give a solution poor in workability.

They should have a number-average molecular weight of 2,000 to 500,000, preferably 5,000 to 300,000. This requirement is met by properly selecting "n" (integer) in the formula [7] given above.

EXAMPLES

The invention will be described below in more detail with reference to Examples and Comparative Examples, which are not intended to restrict the scope thereof. They involve measurement of characteristic properties with the following apparatus.
[1] $^1$H-NMR
  Model: Varian NMR System 400NB (400 MHz) ECP500 (JEOL)
  Solvents: $CDCl_3$ and $DMSO\text{-}d_6$
[2] Mass spectrometry
  Model: LX-1000 (JEOL)
[3] Melting point (m.p.)
  Model: Micro melting point apparatus (MP-S3) (from Yanaco Kiki Kaihatsu Kenkyusho)
[4] X-ray single crystal analysis
  Model: M18XHF/DIP2030 (from Mac Science)
  X-ray: $MoK_\alpha$ (45 kV, 200 mA)
  Measured at room temperature
[5] Molecular weight of polyamic acid or polyimide
  Model: Normal temperature gel permeation chromatograph (GPC) (SSC-7200 from Senshu Kagaku), with Shodex's columns KD803 and 805, and DMF as eluent.
  The number-average and weight-average molecular weights were obtained from calibration curves for polyethylene glycol and polyethylene oxide as the standard reference materials. The resulting polyimide was analyzed by $^1$H-NMR after dissolution in $DMSO\text{-}d_6$ and was examined for the ratio of imidization by calculations from the ratio of the peak area of protons assigned to benzene rings to the peak area of protons assigned to amide residues remaining without being imidized.

Example 1

Synthesis of cis,cis,cis-tetramethyl 1,2,3,4-cyclopentane-tetracarboxylate (cis,cis,cis-TMCP)

[Chemical Formula 22]

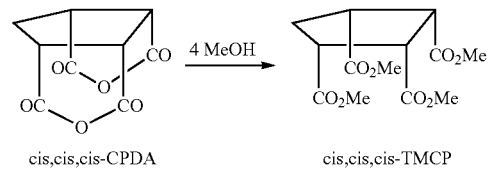

There were placed 17.9 g (85 mmol) of cis,cis,cis-CPDA, 1.79 g of 95% sulfuric acid, and 89.5 g of methanol in a 200-mL four-neck flask of Pyrex (registered trademark) glass. The reactants were heated in an oil bath at 80° C. under reflux for 6 hours. After the completion of reaction, the reaction product was condensed to give an oily substance (29 g). The oily substance was dissolved in ethyl acetate and water, and the organic layer was separated, followed by water washing, concentration, and vacuum drying. Thus there was obtained 21.7 g of colorless oily substance (yields: 84.4%). This oily substance solidified at 25° C.

The resulting crystal was found to be cis,cis,cis-TMCP by $^1$H-NMR analysis.

$^1$H-NMR ($CDCl_3$, δ ppm): 2.398-2.453 (m, 1H), 2.779-2.838 (m, 1H), 3.102-3.127 (m, 2H), 3.404-3.426 (m, 2H), 3.678-3.728 (m, 12H).

Example 2

Synthesis of trans,trans,trans-tetramethyl 1,2,3,4-cyclopentanetetracarboxylate (trans,trans,trans-TMCP)

[Chemical Formula 23]

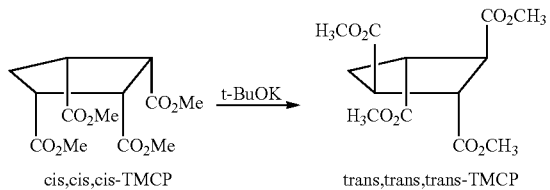

There were placed 9.06 g (30 mmol) of cis,cis,cis-TMCP, 1.01 g (30 mol %) of potassium t-butoxide (95% purity), and 63 g of methanol in a 100-mL four-neck flask of Pyrex (registered trade mark) glass. The reactants were heated in an oil bath at 80° C. under reflux for 2 hours. After the completion of reaction, the reaction product was concentrated and the resulting residue was dissolved in ethyl acetate and water. The resulting solution was ice-cooled and acidified with 35% hydrochloric acid. The organic layer was separated and concentrated to give 8.48 g of crude oily substance (yields: 93.6%). This crude oily substance was purified by silica gel chromatography (eluent: a mixture of ethyl acetate and heptane, from 1/3 to 1/1). Thus there was obtained 6.14 of oily substance (yields: 67.7%).

This oily substance was found to be trans,trans,trans-TMCP by $^1$H-NMR analysis.

$^1$H-NMR (CDCl$_3$, δ ppm): 1.220-1.296 (m, 6H), 2.308 (t, J=8 Hz, 2H), 3.208-3.572 (m, 3H), 3.670-3.747 (m. 3H), 4.105-4.229 (m, 4H).

Example 3

Synthesis of trans,trans,trans-1,2,3,4-cyclopentane-tetracarboxylic acid (trans,trans,trans-CPTC)

[Chemical Formula 24]

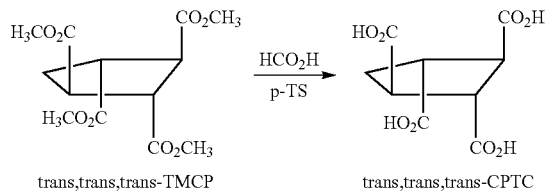

trans,trans,trans-TMCP                    trans,trans,trans-CPTC

There were placed 4.74 g (15.6 mmol) of trans,trans,trans-TMCP, 0.474 g (10 wt %) of p-toluenesulfonic acid monohydrate, and 33.2 g of formic acid in a 100-mL four-neck flask of Pyrex (registered trademark) glass. The reactants were heated at 130° C. under reflux for 7 hours, with methyl formate (by-product) continuously distilled away. After the completion of reaction, the reaction product was concentrated to give 3.60 g of fatty substance. This fatty substance was dissolved with heating in acetonitrile. The resulting solution was concentrated and ice-cooled overnight for precipitation. The resulting white crystals were filtered off and dissolved in a mixture of ethyl acetate and n-heptane (1/1 by volume), followed by washing and vacuum drying. Thus there was obtained 2.30 g of white crystals (yield: 59.9%).

This substance was found to be trans,trans,trans-CPTC by mass spectrometry and $^1$H-NMR analysis.

MASS (ESI$^-$, m/e(%)): 245 ([M-H]$^-$, 100), 227 (57), 183 (18).

$^1$H-NMR (DMSO-d$_6$, δ ppm): 2.033-2.078 (m, 2H), 2.915-2.975 (m, 2H), 3.178-3.195 m, 2H), 12.509 (brs, 4H).

m.p.: 208 to 209° C.

Example 4

Synthesis of "cage" CPDA

[Chemical Formula 25]

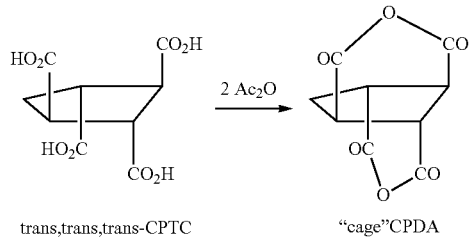

trans,trans,trans-CPTC           "cage"CPDA

There were placed 7.80 g (31.7 mmol) of trans,trans,trans-CPTC and 26.0 g (255 mmol) of acetic anhydride in a 100-mL four-neck flask of Pyrex (registered trademark) glass. The reactants were heated with stirring at a bath temperature of 110° C. for 7 minutes to give a uniform solution. After continued stirring for 10 minutes to complete the reaction, the reaction product was concentrated and the residue was dissolved in DMF with heating. The solution was concentrated to 12.5 g to give a slurry containing crystals. The slurry was given ethyl acetate so that the total amount became 23.4 g. The resulting solution was heated and ice-cooled overnight for precipitation. The precipitates (white crystals) were filtered off, washed with ethyl acetate, and vacuum dried. Thus there was obtained 5.13 g of white crystals (yield: 77.0%).

These crystals were found to be "cage" CPDA by $^1$H-NMR analysis and X-ray structure analysis.

$^1$H-NMR (DMSO-d$_6$, δ ppm): 2.565-2.588 (m, 2H), 3.618-3.646 (m, 2H), 4.239 (t, J=1.2 Hz, 2H)

m.p.: 228 to 230° C.

Results of X-Ray Analysis of "Cage" CPDA Single Crystal

The white crystals of "cage" CPDA obtained as mentioned above were used as such for X-ray analysis of single crystal. The resulting ORTEP diagram is shown in FIG. 1.

Crystallographic parameters

Molecular formula: C$_9$H$_6$O$_6$

Molecular weight: 210.14

Color, shape: colorless, plate

Crystal system: triclinic

Space group: P-1

Crystal form: plane

Lattice constant: a=6.621 (1) Å, b=11.007 (2) Å, c=12.191 (2) Å,

α=79.554°, β=89.969°, γ=72.474°

V=831.8 (2) Å$^3$

Z value=4

D calc=1.513 Mg/m$^3$

Mo K<α> radiation

λ (MoKa)=0.71072 Å

No. of measured reflections=950

No. of observed reflections=885

R=0.06 wR=0.08

Temp.=297K

Example 5

Synthesis of "Cage" CPDA-1,3-BAPB Polyamic Acid and Polyimide

[Chemical Formula 26]

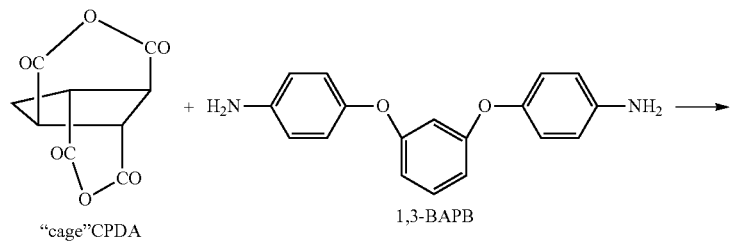

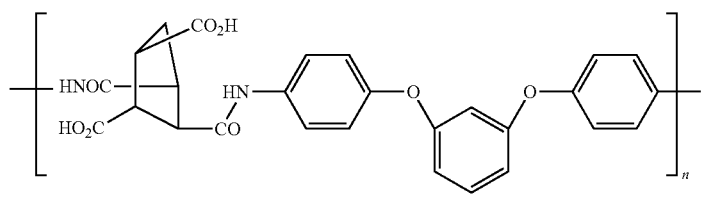

"cage" CPDA/1,3-BAPB Polyamic acid

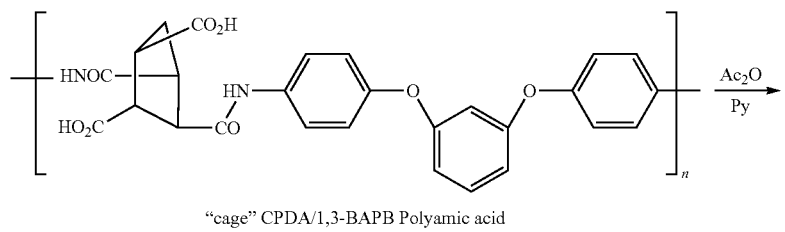

"cage" CPDA/1,3-BAPB Polyamic acid

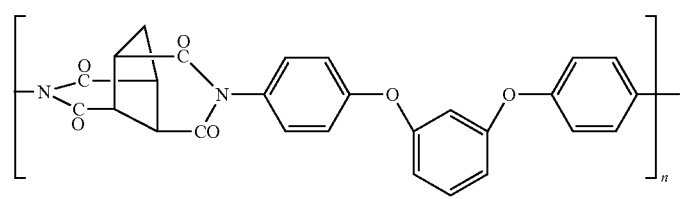

"cage" CPDA/1,3-BAPB Polyamide

There were placed 1.36 g (4.85 mmol) of 1,3-BAPB and 9.60 g of NMP in a 50-mL four-neck flask (equipped with a stirrer) immersed in a water bath at 20° C. The reactant was dissolved by stirring at 185 rpm. With stirring continued, the solution was given 1.02 g (4.85 mmol) of "cage" CPDA in small portions. Stirring was continued at 20 to 17° C., for 24 hours for polymerization. Thus there was obtained a solution of polyamic acid, with a solid content of 20 wt %. This solution was found to have a viscosity of 332 mPa·s. The results of GPC analysis indicate that the polyamic acid has a number-average molecular weight (Mn) of 11,178 and a weight-average molecular weight (Mw) of 23,424, with Mw/Mn being 2.10.

Subsequently, the solution was diluted with NMP (28 g) so that its solid content decreased to 6 wt %. The diluted solution was given 10.2 g (100 mmol) of acetic anhydride, followed by stirring for 5 minutes. The resulting solution was further given 4.75 g (60 mmol) of pyridine, followed by stirring at 100° C. for 5 hours.

After cooling to room temperature, the resulting solution was added dropwise to 200 mL of methanol with stirring. Stirring was continued for 1 hour for precipitation. The precipitated grayish powder was filtered off and washed with 100 mL of methanol three times and finally vacuum-dried at 80° C. for 2 hours. Thus there was obtained 2.0 g of "cage" CPDA-1,3-BAPB polyimide (yields: 88.3%). The ratio of imidization was 79.8% according to the data of $^1$H-NMR analysis.

m.p.: 265 to 270° C.

Example 6

Synthesis of "Cage" CPDA-1,3-BAPB Polyamic Acid and Polyimide

[Chemical Formula 27]

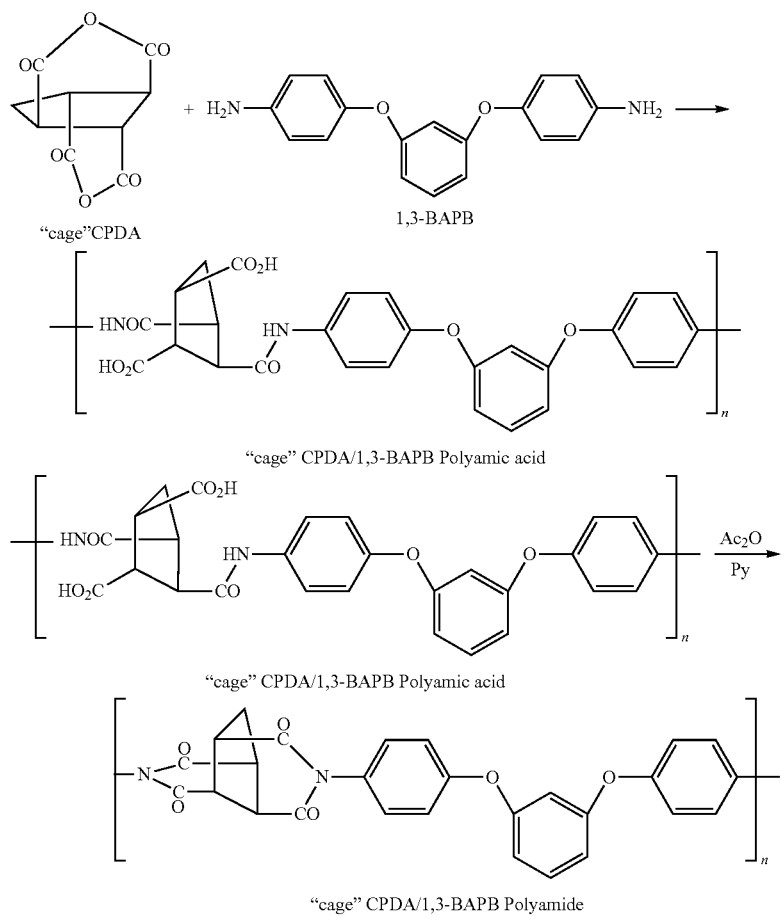

There were placed 1.36 g (4.85 mmol) of 1,3-BAPB and 9.60 g of NMP in a 50-mL four-neck flask (equipped with a stirrer) immersed in a water bath at 20° C. The reactant was dissolved by stirring at 185 rpm. With stirring continued, the solution was given 1.02 g (4.85 mmol) of "cage" CPDA in small portions. Stirring was continued at 50° C., for 24 hours for polymerization. Thus there was obtained a solution of polyamic acid, with a solid content of 20 wt %. This solution was found to have a viscosity of 210 mPa·s. The results of GPC analysis indicate that the polyamic acid has a number-average molecular weight (Mn) of 8,695 and a weight-average molecular weight (Mw) of 16,603, with Mw/Mn being 1.91.

Subsequently, the solution was diluted with NMP (28 g) so that its solid content decreased to 6 wt %. The diluted solution was given 10.2 g (100 mmol) of acetic anhydride, followed by stirring for 5 minutes. The resulting solution was further given 4.75 g (60 mmol) of pyridine, followed by stirring at 110° C. for 5 hours.

After cooling to room temperature, the resulting solution was added dropwise to 160 mL of methanol with stirring. Stirring was continued for 1 hour for precipitation. The precipitated grayish powder was filtered off and washed with 120 mL of methanol three times and finally vacuum-dried at 80° C. for 2 hours. Thus there was obtained 2.0 g of "cage" CPDA-1,3-BAPB polyimide (yields: 88.3%). The ratio of imidization was 77.9% according to the data of $^1$H-NMR analysis. The results of GPC analysis indicate that the polyimide has a number-average molecular weight (Mn) of 8,233 and a weight-average molecular weight (Mw) of 15,067, with Mw/Mn being 1.83.

m.p.: 268 to 270° C.

Example 7

Synthesis of "Cage" CPDA-DPP Polyamic Acid and Polyimide

[Chemical Formula 28]

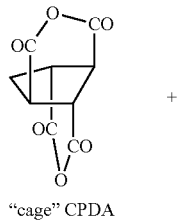

"cage" CPDA

-continued

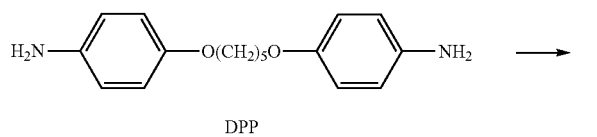

DPP

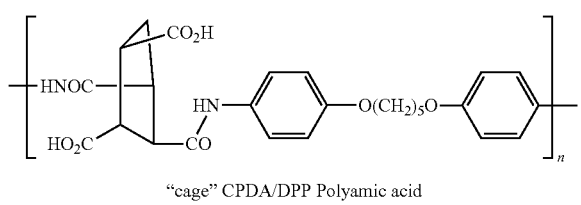

"cage" CPDA/DPP Polyamic acid

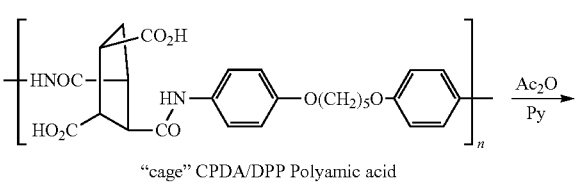

"cage" CPDA/DPP Polyamic acid

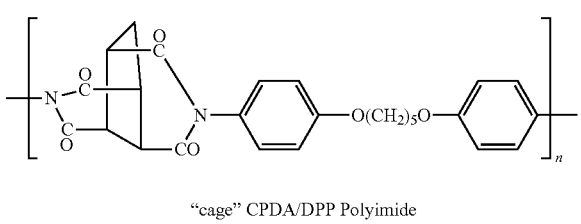

"cage" CPDA/DPP Polyimide

There were placed 1.39 g (4.85 mmol) of 4,4'-diamino-1,5-phenoxypentane (DPP) and 12.2 g of NMP in a 50-mL four-neck flask (equipped with a stirrer) immersed in a water bath at 20° C. The reactant was dissolved by stirring at 185 rpm. With stirring continued, the solution was given 1.02 g (4.85 mmol) of "cage" CPDA in small portions. Stirring was continued at 20 to 17° C., for 24 hours for polymerization. Thus there was obtained a solution of polyamic acid, with a solid content of 20 wt %. The viscosity of this solution was 5,920 mPa·s.

Subsequently, the solution was diluted with NMP (37.4 g) so that its solid content decreased to 6 wt %. The diluted solution was given 10.2 g (100 mmol) of acetic anhydride, followed by stirring for 5 minutes. The resulting solution was further given 4.75 g (60 mmol) of pyridine, followed by stirring at 100° C. for 2 hours.

After cooling to room temperature, the resulting solution was added dropwise to 190 mL of methanol with stirring. Stirring was continued for 1 hour for precipitation. The precipitated grayish powder was filtered off and washed with 60 mL of methanol three times and finally vacuum-dried at 80° C. for 2 hours. Thus there was obtained 2.27 g of "cage" CPDA-DDP polyimide in the form of violet granules (yields: 98.5%). The ratio of imidization was 95.9% according to the data of $^1$H-NMR analysis. The results of GPC analysis indicate that the polyimide has a number-average molecular weight (Mn) of 23,563 and a weight-average molecular weight (Mw) of 77,031, with Mw/Mn being 3.27.

m.p.: 275 to 280° C.

Example 8

Synthesis of "Cage" CPDA-p-PDA Polyamic Acid and Polyimide

[Chemical Formula 29]

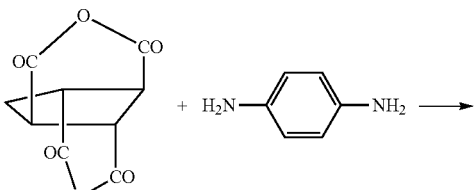

"cage"CPDA         p-PDA

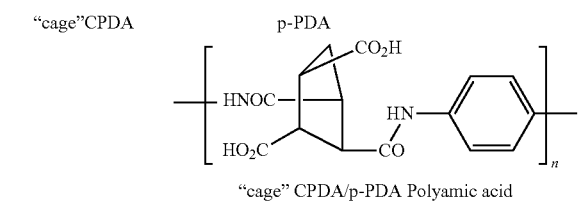

"cage" CPDA/p-PDA Polyamic acid

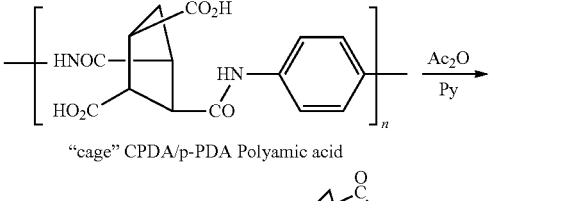

"cage" CPDA/p-PDA Polyamic acid

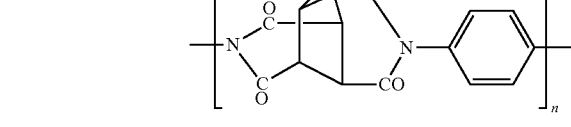

"cage" CPDA/p-PDA Polyamide

There were placed 0.541 g (5.00 mmol) of p-phenylenediamine and 8.2 g of NMP in a 50-mL four-neck flask (equipped with a stirrer) immersed in a water bath at 20° C. The reactant was dissolved by stirring at 185 rpm. With stirring continued, the solution was given 1.05 g (5.00 mmol) of "cage" CPDA in small portions. Stirring was continued at 20 to 17° C., for 24 hours for polymerization. Thus there was obtained a solution of polyamic acid, with a solid content of 20 wt %. This solution was found to have a viscosity of 1,355 mPa·s. The results of GPC analysis indicate that the polyamic acid has a number-average molecular weight (Mn) of 28,448 and a weight-average molecular weight (Mw) of 95,779, with Mw/Mn being 3.37.

Subsequently, the solution was given 10.2 g (100 mmol) of acetic anhydride, followed by stirring for 5 minutes. The resulting solution was further given 4.75 g (60 mmol) of pyridine, followed by stirring at 110° C. for 2 hours. The solution yielded a gel-like substance.

After cooling to room temperature, the resulting solution was added dropwise to 170 mL of methanol with stirring. Stirring was continued for 1 hour to crush the gel-like substance. The precipitated violet gel-like substance was filtered off and washed with 90 mL of methanol three times and finally vacuum-dried at 80° C. for 2 hours. Thus there was obtained 1.48 g of "cage" CPDA-p-PDA polyimide (yields: 100%). The ratio of imidization was 93.8% according to the data of $^1$H-NMR analysis.

m.p.: >300° C.

Example 9

Synthesis of "Cage" CPDA-DDE Polyamic Acid and Polyimide

[Chemical Formula 30]

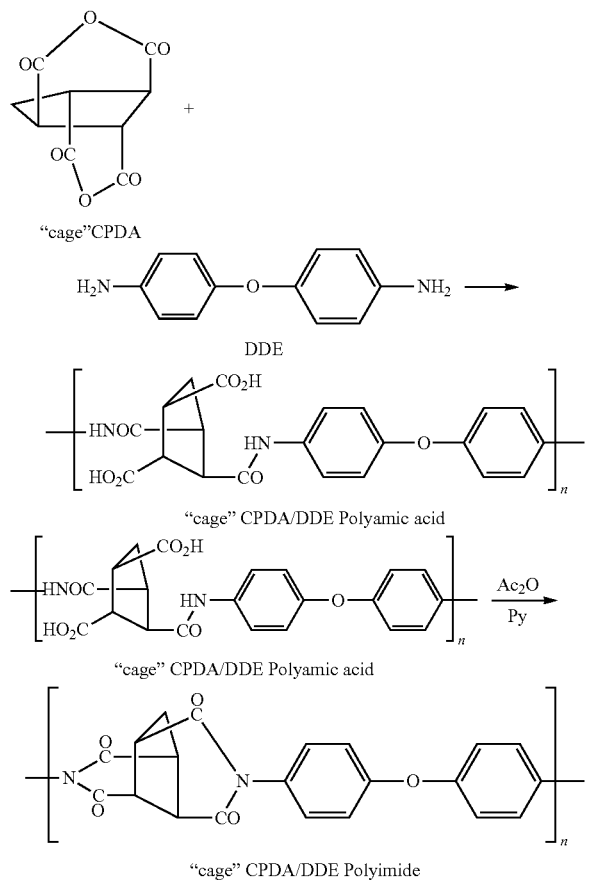

There were placed 1.00 g (5.00 mmol) of 4,4'-diaminodiphenyl ether (DDE) and 8.3 g of NMP in a 50-mL four-neck flask (equipped with a stirrer) immersed in a water bath at 20° C. The reactant was dissolved by stirring at 185 rpm. With stirring continued, the solution was given 1.05 g (5.00 mmol) of "cage" CPDA in small portions. Stirring was continued at 20 to 17° C., for 15 hours. The solution turned into a syrupy viscous solution which wound around the stirrer shaft. After stirring at 50° C. for 2 hours with additional NMP (36.8 g), there was obtained a polyamic acid solution with a solid content of 6 wt %. This solution was found to have a viscosity of 119 mPa·s. The results of GPC analysis indicate that the polyamic acid has a number-average molecular weight (Mn) of 50,129 and a weight-average molecular weight (Mw) of 241,300, with Mw/Mn being 4.81.

Subsequently, the solution was given 10.2 g (100 mmol) of acetic anhydride, followed by stirring for 5 minutes. The resulting solution was further given 4.75 g (60 mmol) of pyridine, followed by stirring at 100° C. for 2 hours. The solution turned into a gel. The gel was made into a uniform solution by heating at 140° C. for 3 hours.

After cooling to room temperature, the resulting solution was added dropwise to 220 mL of methanol with stirring. Stirring was continued for 1 hour for precipitation. The precipitated grayish powder was filtered off and washed with 90 mL of methanol three times and finally vacuum-dried at 80° C. for 2 hours. Thus there was obtained 1.93 g of "cage" CPDA-DDE polyimide (yields: 100%). The ratio of imidization was 95.8% according to the data of $^1$H-NMR analysis.

m.p.: >300° C.

Comparative Example 1

Synthesis of CPDA-1,3-BAPB Polyamic Acid and Polyimide

[Chemical Formula 31]

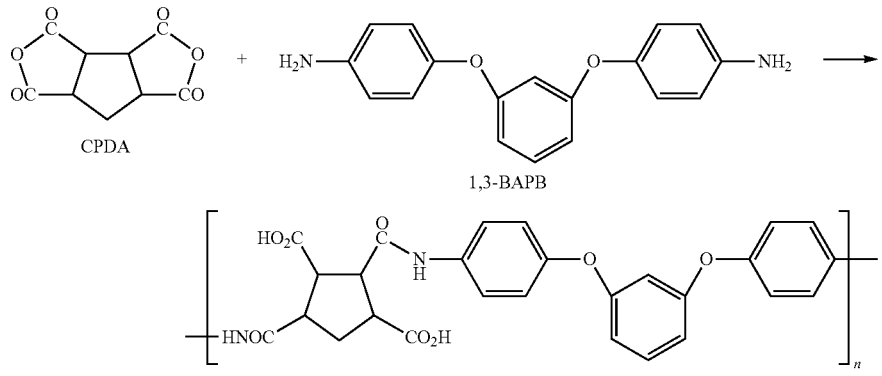

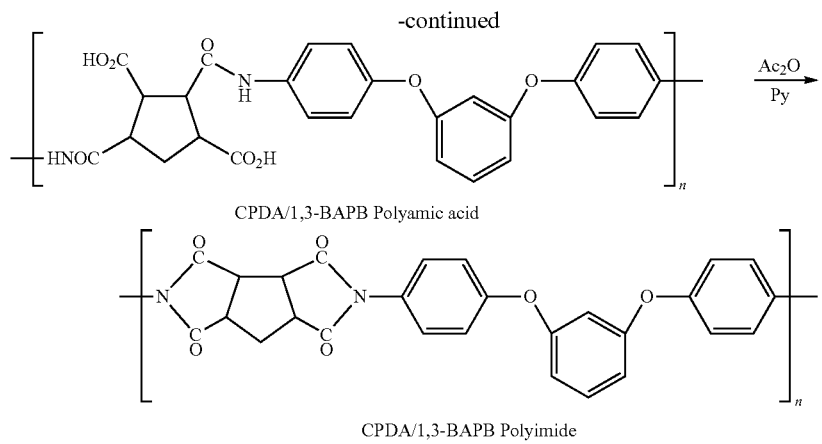

CPDA/1,3-BAPB Polyamic acid

CPDA/1,3-BAPB Polyimide

There were placed 2.79 g (10.00 mmol) of 1,3-BAPB and 19.6 g of NMP in a 50-mL four-neck flask (equipped with a stirrer) immersed in a water bath at 25° C., so that 1,3-BAPB was dissolved in NMP. With stirring continued, the solution was given 2.10 g (10 mmol) of 1,2,3,4-cyclopentanetetracarboxylic acid-1,2:3,4-dianhydride (CPDA) in small portions. The solution was stirred at 25° C. for 24 hours for polymerization. There was obtained a polyamic acid solution with a solid content of 20 wt %. This solution was diluted with DMAc so that the solid content decreased to 8 wt %. The diluted solution was stirred for 5 hours with 10.2 g (100 mmol) of acetic anhydride and further stirred at 100° C. for 2 hours with 7.9 g (100 mmol) of pyridine.

After cooling to room temperature, the resulting solution was added dropwise to 3.5 times as much (in volume) water as the solution with stirring. Stirring was continued for 30 minutes for precipitation. The precipitated white powder was filtered off and washed with water and vacuum-dried at 80° C. for 2 hours. Thus there was obtained 3.8 g of CPDA-1,3-BAPB polyimide (yields: 83.8%). The ratio of imidization was 90.1% according to the data of $^1$H-NMR analysis. The results of GPC analysis indicate that the polyamic acid has a number-average molecular weight (Mn) of 2,421 and a weight-average molecular weight (Mw) of 3,030, with Mw/Mn being 1.25.

m.p.: 193 to 195° C.

Examples and Comparative Example mentioned above show that the polyimide according to the present invention has a higher molecular weight than CPDA polyimide. They also show that the former has a higher melting point (above 260° C.) than the latter (below 200° C.). This implies that the former is superior to the latter in heat resistance.

[Solubility of Polyimide]

The polyimide samples obtained in Examples 5 and 6 and Comparative Example 1 were tested as follows for solubility in various organic solvents shown in Table 1. The results are also shown in Table 1.

<Method for Solubility Test>

The solubility was rated according to the following criteria by observation of each sample (2 mg) added to the organic solvent (0.2 mL) with stirring.

⊚: completely soluble at 25° C. (room temperature)
○: completely soluble at 80° C. (with heating)
Δ: partly soluble at 80° C. (with heating)
x: insoluble at 80° C.

DMSO: dimethylsulfoxide, DMF: N,N-dimethylformamide, THF: tetrahydrofuran

TABLE 1

Solubility of "cage" CPDA-PI in Organic Solvents

| Organic solvent | Example 5 | Example 6 | *Comparative Example 1 |
|---|---|---|---|
| DMSO | ⊚ | ⊚ | ⊚ |
| DMF | ⊚ | ⊚ | ⊚ |
| γ-butyrolactone | ⊚ | ⊚ | Δ |
| m-cresol | ○ | ⊚ | Δ |
| Pyridine | ⊚ | ⊚ | ⊚ |
| 1,4-dioxane | Δ | ⊚ | X |
| THF | X | Δ | X |

⊚: completely soluble at room temperature
○: completely soluble with heating
Δ: partly soluble with heating
X: insoluble with heating It is noted from Table 1 that the sample of "cage" CPDA-1,3-BAPB polyimide obtained in Examples 5 and 6 are more soluble in organic solvents than the sample of CPDA-1,3-BAPB polyimide despite their higher number-average molecular weight (Mn) and weight-average molecular weight (Mw).

The invention claimed is:

1. A polyamic acid which contains the repeating unit represented by the formula [7] below in an amount of at least 10 mol %

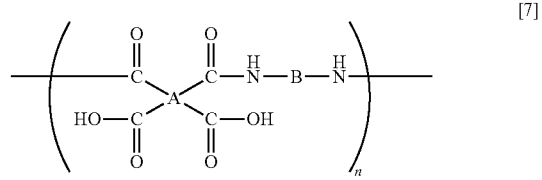

[7]

wherein A denotes a tetravalent organic group represented by the formula [8] and B denotes a divalent organic group and n is an integer

[8]

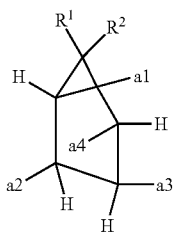

wherein $R^1$ and $R^2$ independently denote a hydrogen atom, halogen atom, or $C_{1-10}$ alkyl group; and a1 to a4 denote the positions for bonding with the carbon atom of the carbonyl group in the formula [7], provided that bonding with the carboxyl group does not take place simultaneously at a1 and a3 and bonding with the carboxyl group does not take place simultaneously at a2 and a4.

2. The polyamic acid as defined in claim 1 wherein said $R^1$ and $R^2$ each is a hydrogen atom or methyl group.

3. The polyamic acid as defined in claim 1 wherein said B is a divalent organic group derived from an alicyclic diamine or aliphatic diamine.

4. The polyamic acid as defined in claim 1 or 2, wherein said B is at least one species selected from the divalent organic groups represented by the formulas [9] to [12]

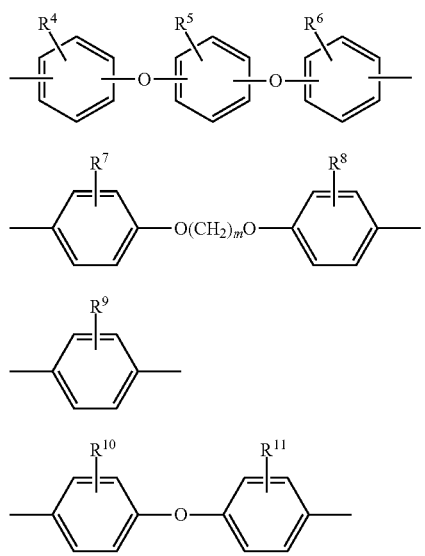

[9]

[10]

[11]

[12]

wherein $R^4$ to $R^{11}$ independently denote a hydrogen atom, halogen atom, or $C_{1-10}$ alkyl group, and m is an integer of 1 to 10.

5. The polyamic acid as defined in claim 4, wherein said B is represented by the formula [13]

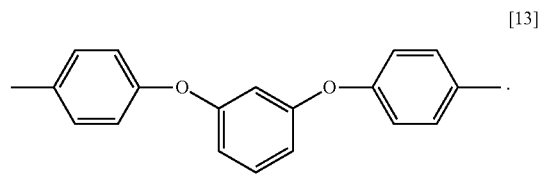

[13]

6. The polyamic acid as defined in claim 4, wherein said B is represented by the formula [14]

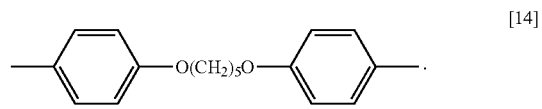

[14]

7. The polyamic acid as defined in claim 4, wherein said B is represented by the formula [15]

[15]

8. The polyamic acid as defined in claim 4, wherein said B is represented by the formula [16]

[16]

* * * * *